United States Patent [19]
Broughton et al.

[11] Patent Number: 5,646,018
[45] Date of Patent: Jul. 8, 1997

[54] BROAD HOST SPECTRUM RHIZOBIACEAE NODULATION SIGNALS

[75] Inventors: William John Broughton, Geneva, Switzerland; Jean Louis Claude Denarie, Castanet-Tolosan; Fabienne Chantal Marie Maillet, Pompertuzat, both of France; Neil Philip John Price, Athens, Ga.; Danielle Jean Claudine Prome; Jean-Claude Adrien Paul Prome, both of Pechbusque, France; Biserka Relic, Geneva, Switzerland; Franck Jean Bernard Talmont, Toulouse, France

[73] Assignees: Institut National de la Recherche Agronomique - I.N.R.A.; Centre National de la Recherche Scientifique - C.N.R.S., both of Paris Cedex, France

[21] Appl. No.: 356,319
[22] PCT Filed: Jun. 29, 1993
[86] PCT No.: PCT/FR93/00653
  § 371 Date: Feb. 1, 1995
  § 102(e) Date: Feb. 1, 1995
[87] PCT Pub. No.: WO94/00466
  PCT Pub. Date: Jan. 6, 1994

[30] Foreign Application Priority Data
Jun. 29, 1992 [FR] France ................. 92 07958
[51] Int. Cl.⁶ .................. C07H 3/06; C12P 19/26; A01N 43/16; A61K 31/715
[52] U.S. Cl. .................. 435/84; 504/117; 504/189; 514/54; 536/123.1
[58] Field of Search .................. 435/84, 100, 101; 536/123.1, 127, 128, 55.1, 55.2; 514/54; 504/117, 189

[56] References Cited
PUBLICATIONS
Bassam et al. (1988) Mol. Plant–Microbe Interactions 1:161–168 Apr. 1988.

*Primary Examiner*—David Guzo
*Assistant Examiner*—Robert Schwartzman
*Attorney, Agent, or Firm*—Oblon, Spivak, McClelland, Maier & Neustadt, P.C.

[57] ABSTRACT

Nod factors of general formula (I):

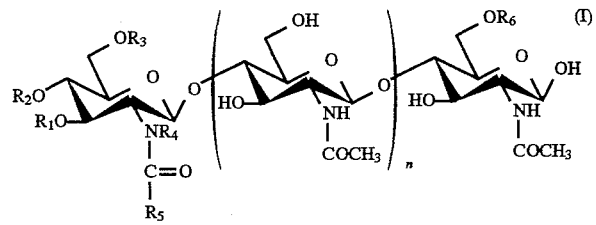

wherein $R_1$, $R_2$ and $R_3$ are hydrogen atom, a carbamyl group or an acetyl group; $R_5$ is the aliphatic chain of a fatty acid; n is 1–4; and one or more of substituents $R_1$, $R_2$ and $R_3$ is a carbamyl group, and/or $R_4$ is a methyl group, and/or $R_6$ is an optionally substituted monosaccharide or oligosaccharide attached to the glucosamin via a glycoside bond.

17 Claims, 1 Drawing Sheet

BROAD HOST SPECTRUM RHIZOBIACEAE NODULATION SIGNALS

BACKGROUND OF THE INVENTION

1. Field of the Invention

The invention relates to the preparation of novel, broad host spectrum nodulation signals (Nod factors).

2. Description of the Related Art

Sol bacteria which belong to the genera Azorhizobium, Bradyrhizobium, Sinorhizobium and Rhizobium, (which are referred to under the general term rhizobia) are capable of interacting with the roots of legumes in order to form nodules in which they fix atmospheric nitrogen. However, only certain combinations of bacteria and plants result in nodulation and host specificity of rhizobia varies greatly [LONG, Cell. 56, 203 (1989)]; [MARTINEZ et al., Crit. Rev. Plant Sci., 23, 483 (1990)]; [DENARIE et al., in Molecular Signals in Plant-Microbe Communications, D.P.S. Verma Ed. pp. 295–324 (CRC Press, Boca Raton, 1992)]. Certain rhizobia (for example *R. leguminosarum* and *R. meliloti*) form nodules on only a small number of legume species, while, on the other hand, others have a broader host spectrum and can form an association with a large number of plants.

Nodule formation results from a coordinated expression of plant genes and bacterial genes. The expression of rhizobial nodulation genes (nod) is controlled by nodD regulator genes whose products are activated by flavonoids which are secreted by the roots of the plants. The ability of the NodD proteins to interact with the plant flavonoids in a specific manner defines a first level of host specificity.

Moreover, two categories of structural nod genes exist: genes which are in common and specific genes. The nod-ABC genes are common to all rhizobia, while nod genes, which are specific to the species, are the major determinants of host specificity.

It has been shown that the common nod genes and the specific nod genes are simultaneously involved in the production of extracellular Nod factors which cause deformation of root hairs in legumes. Some inventors have identified Nod factors, termed NodRm, in *R. meliloti* which factors have a lipo-oligosaccharide structure, whose biosynthesis is under the control of common nodABC genes, and which are glucosamine oligomers linked to each other by β-1,4 bonds, N-acylated on the non-reducing terminal glucosamine and N-acetylated on the other glucosamine residues (Application PCT FR/9100283 in the names of the INSTITUT NATIONAL DE LA RECHERCHE AGRONOMIQUE and the CENTRE NATIONAL DE LA RECHERCHE SCIENTIFIQUE). Host specificity is subsequently determined by the nature of the substituents attached to this skeleton which they have in common. In the case of *R. meliloti*, the function of major host specificity genes (nodH and nodPQ) is to determine the sulfation of these lipo-oligosaccharide factors [ROCHE et al., Cell, 67, 1131 (1991)], while, in the case of *R. leguminosarum*, the nodFE genes control the synthesis of a highly unsaturated lipid residue [SPAINK et al., Nature, 354, 125, (1991)].

The strain Rhizobium sp. NGR234 has a unique place amongst the legume symbionts; it has, in fact, the broadest host spectrum of all known rhizobia, and it is known at present that it causes nodulation of over 60 legume species. Amongst these hosts there are, in particular, most of the commercially important legumes such as, for example, soya bean or groundnut. Rhizobium NGR234 can, moreover, cause nodulation of plants which do not belong to the legumes, such as, for example, Parasponia andersonii.

SUMMARY OF THE INVENTION

The inventors have sought to isolate and identify the Nod factors which are responsible for the broad host spectrum of Rhizohium sp. NGR234 and were able to characterize a novel family of Nod factors termed NodNGR factors. These NodNGR factors are lipooligosaccharides which belong to the same family as the NodRm factors which have already been described by some of the inventors (Application PCT FR/9100283), but also have structural characteristics which allow them to be distinguished from Nod Rm factors.

Firstly, their reducing terminal glucosamine residue is substituted on the C6 by a different sugar;

Secondly, their non-reducing terminal glucosamine can be esterified by one or more carbamoyl groups;

Thirdly, the nitrogen atom which is substituted by the long-chain fatty acid is also methylated.

Moreover, the inventors have studied the structure of the Nod factors produced by a range of strains of the Rhizobiaceae from very different geographical origins and which are symbionts of a very wide range of hosts, such as *Rhizobium tropici* which forms nodules on beans and Leucaena, *Sinorhizobium fredii*, which forms nodules on soya beans and *Azorhizobium caulinodans* which is a symbiont of Sesbania. They found that the Nod factors produced by these different strains had at least one of the structural features observed for the NodNGR factors such as the presence of a sugar on the reducing terminal glucosamine (*Sinorhizobium fredii, Azorhizobium caulinodans, Rhizobium phaseoli*) or of an N-methyl group on the non-reducing terminal glucosamine (*Rhizobium tropici, Azorhizobium caulinodans*).

The novel Nod factors of the invention, which show at least one of the three structural characteristics mentioned hereinabove, will generally be termed hereinafter NodNGR-type Nod factors.

DESCRIPTION OF THE PREFERRED EMBODIMENTS

Figure 1:
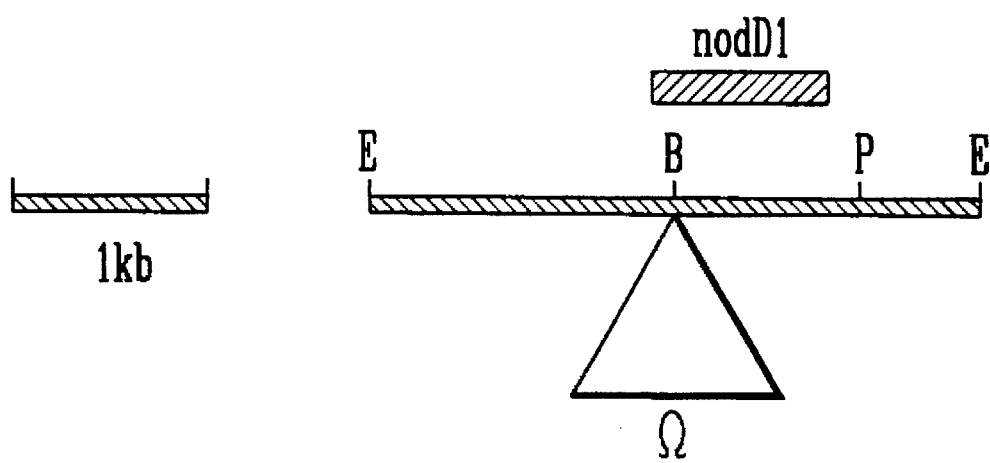
FIG. 1 depicts the restriction map of the Eco RI fragment containing the nodD1 region from NGR234.

More particularly, the NodNGR-type Nod factors obtained from NGR234 will hereinbelow be termed NodNGR factors. Nod factors obtained from other strains studied by the inventors and having at least one of these characteristics represent NodNGR-type Nod factors. It seems that the source of NodNGR-type Nod factors can be very varied.

The present invention relates to Nod factors of the general formula (I) hereinbelow:

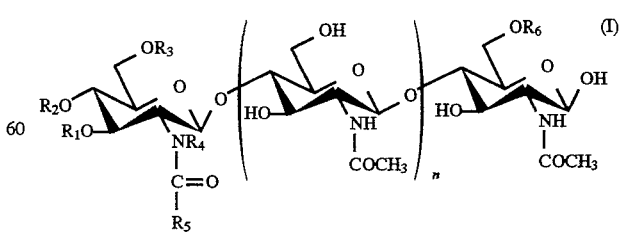

in which:

$R_1$, $R_2$ and $R_3$ represent a hydrogen atom, a carbamoyl group or an acetyl group;

$R_5$ represents the aliphatic chain of a fatty acid;
n is between 1 and 4, and wherein:
  one or more of the substituents $R_1$, $R_2$ or $R_3$ is a carbamoyl group, and/or
  $R_4$ represents a methyl group, and/or
  $R_6$ represents a monosaccharide or an oligosaccharide, optionally substituted, and linked to the glucosamine by a glycosidic linkage.

In a preferred embodiment of the present invention, $R_5$ represents the aliphatic chain of a $C_{10-24}$-, preferably a $C_{14-20}$-, fatty acid.

In a preferred form of this embodiment, $R_5$ is the aliphatic chain of vaccenic acid or palmitic acid.

Vaccenic acid and palmitic acid are major substituents found in preparations of NodNGR factors from Rhizobium NGR234; however, a large number of different fatty acids varying as much with regard to the number of carbon atoms of the aliphatic chain as by the degree of unsaturation, or by the presence of substituents such as hydroxyl groups on said aliphatic chain, was observed; no effect of these variations on the activity of the NodNGR factors was found by the inventors.

In yet another preferred embodiment of the present invention, $R_6$ is selected from the monosaccharide group comprising optionally substituted fucose and optionally substituted arabinose.

In an advantageous arrangement of this embodiment, $R_6$ has the general formula (II):

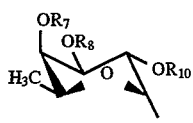

(II)

in which:
  $R_7$ and $R_8$ represent a hydrogen atom, an acetyl group or a sulfate group,
  $R_{10}$ represents a hydrogen atom or a methyl group.

In a preferred form of this arrangement, $R_7$ is a hydrogen atom and $R_8$ a sulfate group.

In another preferred form of this arrangement, $R_7$ is an acetyl group and $R_8$ a hydrogen atom.

In yet another preferred form of this arrangement, both $R_7$ and $R_8$ are hydrogen atoms.

The NodNGR factors belong to the same family of molecules as the NodRm factors which have been purified from *R. meliloti*: all have in common the skeleton of D-glucosamine residues linked to each other by β-1,4 linkages, are N-acylated on the non-reducing terminal glucosamine and N-acetylated on the other residues. These structural similarities tie in with the observations made before by some of the inventors and confirm that, in all rhiozobia, the function of the nodABC genes is to control the synthesis of a skeletal structure of N-acylated and N-acetylated oligochitosan. The work carried out by the inventors therefore reveals that the Nod factors of all Rhizobiaceae belong to the same chemical family.

In the NodRm factors, the fatty acid chain contains at least one conjugated double bond which seems to play an essential role in the induction of nodular meristems; in contrast, the NodNGR factors are N-acylated with vaccenic acid or palmitic acid and therefore do not have a conjugated double bond. The nitrogen atom which is substituted by a long-chain fatty acid is also methylated in the NodNGR factors. These observations allow the hypothesis to be put forward that certain biological activities of the Nod-type lipo-oligosaccharides require a certain structural configuration at the joint between the lipid part and the saccharide skeletal structure. These structural conditions would be provided in one case by the conjugated double bond and, in the other case by the N-methyl group.

The family of the NodNGR factors is very large. Mass spectrometry analysis using fast-atom bombardment ionization (FAB-MS) and also nuclear magnetic resonance analysis have shown that the following variations exist in the substituents:

1) The 2-O-methylfucose residue can be unsubstituted or else sulfated on O-3 or acetylated on O-4;

2) The nitrogen atom of the non-reducing terminal glucosamine can be acylated by palmitic acid or else by vaccenic acid;

3) The number of carbamoyl substituents on the non-reducing terminal glucosamine varies between zero and two.

The combinations of these possible different substituents lead to at least 18 (=3×2×3) possible structures if the carbamoyl substitution sites are fixed and their number may even be greater to the extent that the carbamoyl group substitution site, or sites, can vary between positions O-3, O-4 and O-6. It is reasonable to assume that it is in particular this structural diversity which is responsible for the broad host spectrum of the NodNGR factors.

The invention also relates to rhizobia strains which overproduce NodNGR type factors, which comprise at least one recombinant plasmid expressing a regulator gene nodD from NGR234 and in particular a rhizobium strain NGR234 which overproduces Nod factors, which strain is obtained by introducing, into NGR234, a recombinant multicopy plasmid termed pA28 which expresses a regulator gene nodD from NGR234, so as to increase the number of copies of this gene, which results in an at least 10-fold increase of the amount of Nod factors produced.

The invention also encompasses recombinant plasmids carrying the regulator gene nodD1 from NGR234, in particular plasmid pA28, which results from inserting an EcoRI-PstI fragment from plasmid pNGRH6 [BASSAM et al. Mol. Plant-Microbe Interact, 1, 161, (1988)], which carries the nodD1 region from NGR234, into plasmid pRK7813 [JONES and GUTTERSON, Gene, 61, 299–306, (1987)].

The invention also relates to a process for the preparation of NodNGR factors, or NodNGR-type factors, which process comprises a step in which at least one strain of rhizobia producing said Nod factors is cultured.

Preferably, a strain will be chosen into which a plasmid according to the invention has been introduced.

In a preferred embodiment of the preparation process of NodNGR-type factors according to the invention, it comprises, moreover, a step in which one or more fractions comprising said factors are extracted from said culture of rhizobia strains.

In a preferred arrangement of this embodiment, the NodNGR factors are extracted from culture supernatant by reverse-phase chromatography, by absorption on a silica column to which hydrophobic groups, such as octadecyl residues, are grafted, followed by elution with methanol.

The present invention also relates to a plant treatment agent comprising, as active ingredient, at least one NodNGR factor or NodNGR-type factor as defined further above, which can be used in particular:

as an agent for stimulating symbiotic properties of legumes, especially with regard to nitrogen fixation;
  as an agent for stimulating the defence mechanisms of plants against pathogene.

Said plant treatment agent preferably comprises a mixture of NodNGR factors and/or NodNGR-type factors. It can advantageously also comprise other Nod factors, for example NodRm-type factors.

In an advantageous embodiment of the plant treatment agent according to the present invention, the composition is included in a solid carrier, such as granules, or else formulated in the form of a coating composition for seed or an aqueous solution or suspension for spraying, in which a Nod factor or Nod factors, according to the invention are present alone or in association with other components, such as, for example, other Nod factors.

In another advantageous embodiment of the plant treatment agent according to the present invention, a Nod factor, or each of the ingredients of a mixture of Nod factors, according to the invention are present in the coating compositions or in the aqueous solutions or suspensions at a concentration of between $10^{-6}$M and $10^{-14}$M.

Moreover, the present invention relates to a therapeutic agent comprising, as active ingredient, at least one NodNGR factor or NodNGR-type factor as defined further above.

In an advantageous embodiment of this therapeutic agent, said factor is present in the therapeutic agent at a concentration of between $10^{-4}$M and $10^{-8}$M.

Besides the above arrangements, the invention also encompasses other arrangements which will emerge from the description which follows.

It must be understood, however, that these examples as well as the appended drawings are given only by way of illustrating the subject of the invention but without imposing any limitation whatsoever.

EXAMPLE 1

PRODUCTION OF A STRAIN OF RHIZOBIACEAE BACTERIA WHICH OVERPRODUCE NodNGR FACTORS

Strain NGR234 and its DNA were engineered as described by BROUGHTON et al. (Arch. Microbial. 141, 14 (1985)) and PERRET et al. (Proc. Natl. Acad. Sci. 88, 1923 (1991)), or by means of traditional techniques (J. SAMBROOK et al., Molecular Cloning. A Laboratory Manual, Cold Spring Harbor Laboratory Press, Cold Spring Harbor (1989)).

A 2.9 kb EcoR1 fragment containing the nodD1 region from NRG234 was excised from plasmid pNGRH6 [BASSAM et al., Mol., Plant-Microbe Interact. 1, 161, (1988)] and then digested with Pst1. The resulting 2.2 kb EcoR1-Pst1 fragment was cloned into pRK7813 at the Pst1 site to give plasmid pA28. pA28 is reintroduced into Rhizobium sp. NGR234 (Rif$^R$) by means of conjugation. The resulting strain NGR(pA28) overproduces Nod factors. It is Nod$^+$ on L. leucocephala, M. atropurpureum, and V. unguiculata. FIG. 1 shows the restriction map of the EcoR1 fragment. The restriction sites are designated as follows:

| B = BamH1, | C = Cla1, | E = EcoR1, |
|---|---|---|
| P = Psi1, | S = Sst1. | |

EXAMPLE 2

PURIFICATION OF THE NodNGR FACTORS

The bacteria NGR234 or NGR234(pa28) are cultured at 27° C. on B+D medium (W. J. BROUGHTON and M. J. DILWORTH, Biochem. J. 125, 1075 (1971)) containing 12 mM succinate, 6 mM glutamate, 1 ml/litre of GAMBORG's Vitamin B5 solution (Sigma, St. Louis, Mo.) (=RMM3) to the end of the logarithmic phase.

For analysis by thin-layer chromatography, 30 ml of cultured bacteria (NGR 234) are induced using $10^{-6}$M of apigenin, which induces the expression of the nodD genes from NGR234, in the presence of 1 μCi/ml of sodium sulfate labeled with sulfur-35, or sodium acetate labeled with carbon-14.

The supernatants are extracted on SEPPAK $C_{18}$ cartridges (Waters Assoc., Milford, Mass.), washed with distilled water and eluted using methanol. The concentrated methanol extracts are applied to silica gel 60 G plates (MERCK, DARMSTADT); chromatography is carried out in a chloroform: methanol: 5M NH$_4$OH (5:4:1 by volume) mixture, and the plate is placed on a FUJI RX film (Fuji Photo Film Co, TOKYO).

Induction of nod genes by $10^{-6}$M apigenin in the presence of $^{14}$C-labeled acetate or $^{35}$S-labeled sulfate results in two radioactive spots on the TLC plates. Extraction of the active principles contained in each of these spots allows substances to be obtained which cause deformation of the root hairs of Macroptilium. This demonstrates that NGR234 secretes sulfur-containing Nod factors. On the other hand, no spot obtained from an NGR234 derivative can be detected in which the nodABC genes have been deleted. Moreover, if the number of copies of the nodD1 gene (regulator gene) is increased by introducing plasmid pA28 into NGR234, an increased production of Nod factors is observed, the Mount produced being multiplied by a factor of 5 to 10.

For chemical analysis, the Nod factors were isolated from the culture supernatant of NGR234 containing plasmid pA28, following induction with apigenin. This production on a larger scale is effected using 50 litres of NGR234(pa28) bacterial culture which has previously been induced with apigenin in RMM3 medium. The lipophilic material is recovered on a $C_{18}$ reversed-phase column (LICHROSORB-18, 40 μ, MERCK, DARMSTADT). The column is washed with 50 times its volume of distilled water and eluted with 10 volumes of methanol. The methanolic solution is evaporated in vacuo and diluted with 100 ml of distilled water. After filtration, the aqueous solution is extracted using 50 ml of ethyl acetate to extract, in particular, apigenin. The aqueous solution is concentrated, and the water-soluble constituents are separated by preparative HPLC on a $C_{18}$ reversed-phase column. Elution is monitored at 206 nm. The solvent is a gradient of acetonitrile in water.

Two major peaks termed fractions A and B were collected in this way. Fraction A (0.3 mg/l of the starting culture) co-elutes with the material originating from the culture labeled with sulfur-35, while fraction B (0.5 mg/l of the original culture) is not labeled under these conditions. The comparison of biological activities of these two fractions is described hereinbelow in Example 4.

EXAMPLE 3

CHARACTERIZATION OF THE NodNGR FACTORS

Hydrolysis with trifluoroacetic acid (4M for 4 hours at 100° C.) of each of the two fractions liberates sugars and fatty acids. The sugars were identified as D-glucosamine, N-methyl-D-glucosamine and 2-O-methyl-L-fucose, either by gas chromatography, mass spectrometry, (GC-MS) of their alditol acetate derivatives, or else by gas chromatographic analysis of their (+)-2-butanolglycosides. Two acids were identified: the largest component as being vaccenic acid (11-Z-octadecenoic acid), while the minor component (approximately 20% of the total) was identified as palmitic acid. The existence of a skeleton which they have in common and which is composed of pentameric N-acetylglucosamine oligomers having a plurality of substituents was deduced from the FAB mass spectrum, which reveals series of ions separated by 203 mass units (molar mass of an N-acetylglucosamine residue).

Fraction A is a mixture of a plurality of sulfated compounds, as confirmed by the ease with which the $SO_3$ radical is lost in positive ionized form. The molecular weight of the major component, deduced from the spectrum of negative ions, is 1595. Other components with a mass of less than 43 or 26 mass units, or a combination of the two, were detected. This latter difference corresponds to the difference between the molecular weight of vaccenic acid and the molecular weight of palmitic acid. Equally, the difference of 43 mass units, which was repeated twice, was attributed to the presence or absence of additional CO—NH groups (carbamoyl residues). The fact that this pattern of three peaks which are separated by 43 mass units accompanied by satellite peaks at a distance of 26 mass units is observed each time a glycosidic linkage is ruptured in the form of positive ions (formation of oxenium ions) justifies the localization of carbamoyl groups of the non-reducing terminal glucosamine. Moreover, if the mass of the oxenium ions of m/z 440, 483 and 526 is subtracted from the mass of a vaccenyl residue (ketene) and, if appropriate, the mass of zero, one or two carbamoyl groups (43 mass units), the mass of the oxenium ion of a methylglucosamine is obtained. This allows the N-methylglucosamine to be localized at the non-reducing end of the oligosaccharide.

Fraction B is also a mixture. Two major components were identified (molecular weights 1557 and 1515, respectively). The difference of 42 mass units between these two components suggests that the second is a monoacetylated form of the first. On the other hand, as in fraction A, other components in which the mass is lower than 43 or 26 mass units are also present. As in the case of the components of fraction A, the carbamoyl groups are localized on the non-reducing terminal N-methylglucosamine which has carries the N-acyl group. In contrast, the additional acetyl group, which is not present in any of the oxenium ions observed, is localized near the reducing end.

The carbon-13 NMR spectrum is compatible with the presence of carbamoyl groups ($\delta$=161.09, 160.62 and 159.80 ppm) and the presence of the other substituents described above. The proton NMR spectrum attributes $\beta$ configurations to the linkages between glucosamines and $\alpha$ configurations for the linkage between 2-O-methylfucose and the reducing glucosamine. The COSY spectrum shows a correlation between the H-5 of the fucose and a deshielded proton $\delta$=4.53 ppm in the case of the compounds of fraction B. This allows the position of the acetyl group to be attributed to the 0-4 position of 2-O-methylfucose. In parallel, the COSY spectrum of the compound of fraction A shows a correlation between the H-2 of 2-O-methylfucose (3.67 ppm) and the deshielded H-3 proton at $\delta$=4.65 ppm, which allows the sulfate group to be localized at the O-3 of 2-O-methylfucose. This latter attribution is confirmed by analysis of the sugars obtained by hydrolysis of the reduced and permethylated fraction A, which shows the presence of dimethyl-2,4-fucose. Moreover, by identifying trimethyl-1,2,3,5-glucosaminitol in the hydrolysis products of the reduced and permethylated fractions A and B, it can be confirmed that the methylfucose is linked glycosidically to the O-6 of the reducing glucosamine. Finally, this analysis also shows 1–4 linkages between the various glucosamines. Since the methylation conditions result in the simultaneous elimination the ester groups (acetates and carbamates), the position of these groups cannot be determined by this method. However, the major components of fractions A and B are bicarbamylated while the types which lack carbamoyl substituents are in the minority.

EXAMPLE 4

TEST FOR GROWTH OF ROOT HAIRS (Hai) AND DEFORMATION OF ROOT HAIRS (Had) CAUSED BY NOD-SULFATED AND NON-SULFATED FACTORS FROM RHIZOBIUM NGR234 ON MACROPTILIUM ATROPURPUREUM, MEDICAGO SATIVA, VICIA SATIVA AND VIGNA UNGUICULATA

The two fractions A and B, (sulfated and non-sulfated) were separated by a reverse-phase HPLC chromatography following the protocol described in Example 2 and were tested separately for their biological activity.

The Had test (deformation of root hairs) on *M. sativa* and Hai test (proliferation and bending of the root hairs) on *V. sativa* were carried out as described by ROCHE et al. [Cell., 76, 1131 (1991)]. In the Bad tests on Macroptilium and Vigna, sterile plantlets are placed into modified Eppendorf tubes (with the cap and part of the bottom removed), and the Eppendorf tubes containing the plantlets are suspended into test tubes whose bottom is painted black in order to protect the roots from light, in such a manner that the root tip is in contact with 10 ml of B+D medium. After incubation for 60 hours (16-hour day, 30° C.; 8-hour night, 20° C.), the roots are removed, stained with Methylene Blue and examined under an inverted microscope. Those root systems which clearly show branching or bending (prolific ramifications or bending at more than one point in the root system) are termed Had$^+$. Those roots which are covered in root hairs are termed Hai$^+$. 10 plants were used for each treatment and dilution. Moreover, 40 (Macroptilium and Vigna) and 60 (Medicago and Vicia) plantlets are used as control plants (grown on medium only) in order to estimate the intrinsic variability of the characters Bad and Hai between one plant and another.

The results are shown in Table I hereinbelow. These results show the number of plants (above 10) which show a positive Bad or Hai activity. The numbers are followed by $^s$ if the ratio of Had$^+$ or Hai$^+$ is significantly higher (probability P=0.05) in the treated plants than in the controls (analyzed using the Fisher test).

NodRm-IV (Ac,S) is the major sulfated Nod factor of strain *R. meliloti* 2011. It is used as positive control for Bad activity on Medicago.

NodRm-IV(Ac) is a non-sulfated Nod factor of NodH$^-$ mutants of *R. meliloti*. It is used as positive control for Hai activity on Vicia.

TABLE 1

| | CONCENTRATION Nod FACTOR (M) | | | | | | |
|---|---|---|---|---|---|---|---|
| | $10^{-7}$ | $10^{-8}$ | $10^{-9}$ | $10^{-10}$ | $10^{-11}$ | $10^{-12}$ | $10^{-13}$ |
| Macroptilium (Had) | | | | | | | |
| NodNRG sulfated | nt | $10^s$ | $10^s$ | $7^s$ | $3^s$ | 0 | |
| NodNGR non-sulfated | nt | $10^s$ | $9^s$ | $4^s$ | 1 | 0 | |
| Vigna (Had) | | | | | | | |
| NodNRG sulfated | $10^s$ | $10^s$ | $10^s$ | $10^s$ | $10^s$ | $9^s$ | $6^s$ |
| NodNGR non-sulfated | $10^s$ | $10^s$ | $10^s$ | $8^s$ | $5^s$ | 4 | nt |
| Medicago (Had) | | | | | | | |
| NodNRG sulfated | $9^s$ | $8^s$ | $9^s$ | $5^s$ | $3^s$ | 1 | |
| NodNGR non-sulfated | $5^s$ | 1 | 2 | 0 | 1 | 1 | |
| NodRM-IV (AC,S) | nt | $9^s$ | $8^s$ | $7^s$ | $6^s$ | $4^s$ | |
| Vicia (Hai) | | | | | | | |
| NodNRG sulfated | $4^s$ | $5^s$ | $3^s$ | 0 | 0 | 0 | |
| NodNGR non-sulfated | $10^s$ | $10^s$ | $9^s$ | $2^s$ | 0 | 0 | |
| NodRM-IV (Ac) | nt | $10^s$ | $10^s$ | $8^s$ | $2^s$ | 0 | | nt = non tested

In root hair deformation tests (Had) carried out with host plants of NGR234, the two groups of NodNGR factors are active at concentrations of as little as $10^{-10}$M/$10^{-11}$M in Macroptilium and $10^{-11}$M/$10^{-12}$M in Vigna. Moreover, in Vigna, the NodRm factors induce not only deformations of the hairiness of the roots, but also of the appearance of a large number of root hairs, as well as bending of the root hairs (Hai).

The sulfated NodRm factors obtained from *R. meliloti* are Had⁺ in *Medicago sativa*, and Hai⁻ in *Vicia sativa* supsp. nigra. In contrast, the non-sulfated NodRm factors secreted by NodH⁻ mutants of *R. meliloti* are Had⁻ in Medicago and Hai⁺ in Vicia. Interestingly, sulfated and non-sulfated Nod-NGR factors have a biological activity on both legumes. In Medicago, the sulfated NodNGR factors are 10,000 times more active than the non-sulfated factors and cause deformation of the hairiness of the roots at concentrations of less than $10^{-11}$ mole. The sulfated NodNGR factors differ from the sulfated NodRm factors with regard to a large number of criteria: for example, the presence of carbamoyl groups and of a methylfucose residue, localization of the sulfate group on the fucose instead of the glucosamine, the absence of a conjugated double bond on the acyl chain which substitutes the nitrogen, and the presence of a methyl group which substitutes the nitrogen. However, both types of factors are active in Medicago, and their activity decreases by a factor of approximately 10,000 when the sulfate group is removed, which demonstrates that Medicago is highly sensitive to sulfated Nod factors. In contrast, in Vicia, the non-sulfated compounds are more active, and deformation of the hairiness of the roots is observed at concentrations of less than $10^{-11}$M.

We claim:
1. A NodNGR-type factor of the following formula (I):

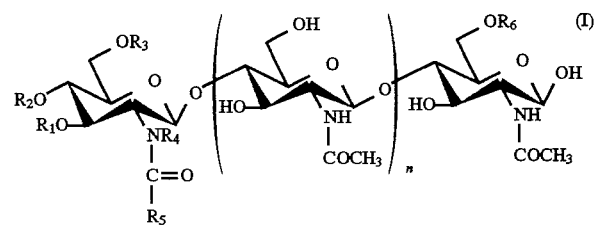

in which:

$R_1$, $R_2$ and $R_3$ represent a hydrogen atom, a carbamoyl group or an acetyl group;

$R_5$ represents the aliphatic chain of a fatty acid;

n is between 1 and 4, and wherein:
  one or more of the substituents $R_1$, $R_2$ or $R_3$ is a carbamoyl group, and/or
  $R_4$ represents a methyl group, and/or
  $R_6$ has the general formula (II)

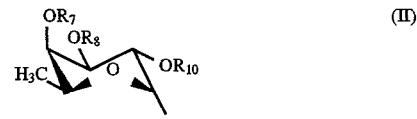

in which:

$R_7$ and $R_8$ represent a hydrogen atom, an acetyl group or a sulfate group, $R_{10}$ represents a hydrogen atom or a methyl group.

2. The Nod factor as claimed in claim 1, wherein $R_5$ represents the aliphatic chain of a $C_{10-24}$ fatty acid.

3. The Nod factor as claimed in claim 1, wherein $R_7$ is a hydrogen atom and $R_8$ is a sulfate group.

4. The Nod factor as claimed in claim 1, wherein $R_7$ is an acetyl group and $R_8$ is a hydrogen atom.

5. The Nod factor as claimed in claim 1, wherein both $R_7$ and $R_8$ are hydrogen atoms.

6. A process for the preparation of NodNGR-type factors as claimed in claim 1, which process comprises a step in which at least one strain of Rhizobiaceae producing said Nod factors in cultured, and a step in which said NodNGR factors are purified from the culture.

7. Plant treatment agent, which comprises, as active ingredient, at least one NodNGR-type factor or a mixture of NodNGR-type factors as claimed in claim 2.

8. The Nod factor as claimed in claim 2, wherein $R_5$ is the aliphatic chain of vaccenic acid or palmitic acid.

9. The Nod factor as claimed in claim 2, wherein $R_5$ represents the aliphatic chain of a $C_{14-20}$ fatty acid.

10. The process as claimed in claim 6, wherein said strain is a strain which overproduces Nod NGR factors and comprises at least one plasmid encoding nodD1 from Rhizobium, Azorhizobium, Bradyrhizobium or Sinorhizobium.

11. The plant treatment agent as claimed in claim 7, which comprises, additionally, other Nod factors.

12. The plant treatment agent as claimed in claim 7, which is included in a solid carrier or formulated in the form of a coating composition for seed or an aqueous solution or suspension for spraying.

13. The plant treatment agent as claimed in claim 7, wherein the NODNGR-type factor or each of the ingredients of the mixture of NodNGR-type factors is present at a concentration of between $10^{-6}$M and $10^{-14}$M.

14. The process as claimed in claim 10, wherein the plasmid results from inserting an Eco I-Pst I fragment of plasmid pNGRH6 comprising the regulator gene nodD1 from strain NGR234 into plasmid pRK7813.

15. A strain of Rhizobiaceae which overproduces NodNGR-type factors for carrying out the process as claimed in claim 10, which comprises at least one recombinant plasmid which results from inserting an EcoRI-PstI fragment of plasmid pNGRH6 comprising a regulator gene nodD1 from strain NGR234 into plasmid pRK7813.

16. The process as claimed in ether of claims 6 or 14, which comprises, moreover, a step in which one or more fractions comprising the NodNGR-type factors are extracted from said culture of Rhizobiaceae.

17. The process as claimed in claim 16, wherein the NodNGR-type factors are extracted from culture supernatant by absorption onto a silica column to which hydrophobic groups are grafted, following by elution with methanol.

* * * * *